(12) United States Patent
Lee et al.

(10) Patent No.: US 8,470,209 B2
(45) Date of Patent: Jun. 25, 2013

(54) PASTE COMPOSITION

(75) Inventors: Eun Sung Lee, Seoul (KR); Sang Cheol Park, Seoul (KR); Won Cheol Jung, Seoul (KR); Jin Young Bae, Seoul (KR)

(73) Assignees: Samsung SDI Co., Ltd., Yongin-si (KR); Samsung Electronics Co., Ltd., Suwon-si (KR)

( * ) Notice: Subject to any disclaimer, the term of this patent is extended or adjusted under 35 U.S.C. 154(b) by 388 days.

(21) Appl. No.: 12/769,206

(22) Filed: Apr. 28, 2010

(65) Prior Publication Data

US 2010/0207077 A1 Aug. 19, 2010

Related U.S. Application Data

(63) Continuation of application No. 11/561,037, filed on Nov. 17, 2006, now abandoned.

(30) Foreign Application Priority Data

Jun. 23, 2006 (KR) .................. 10-2006-0056909

(51) Int. Cl.
*H01B 1/12* (2006.01)
*B82Y 30/00* (2006.01)

(52) U.S. Cl.
CPC .................................... *B82Y 30/00* (2013.01)
USPC .................... 252/519.3; 252/518.1; 564/353; 564/354

(58) Field of Classification Search
USPC ..................... 252/518.1, 519.3; 564/353, 354
See application file for complete search history.

(56) References Cited

U.S. PATENT DOCUMENTS

| | | | |
|---|---|---|---|
| 3,440,029 A | 4/1969 | Little et al. | |
| 4,368,186 A | 1/1983 | Vickery et al. | |
| 4,602,016 A | 7/1986 | Cross et al. | |
| 7,626,115 B2 | 12/2009 | Lee et al. | |

FOREIGN PATENT DOCUMENTS

| | | |
|---|---|---|
| EP | 0 269 363 A2 | 11/1987 |
| JP | 2002-050413 | 2/2002 |
| KR | 1020050082624 | 8/2005 |
| RO | 78653 A2 | 4/1982 |

OTHER PUBLICATIONS

Jianu, CA 99:177867, 1983.

*Primary Examiner* — Mark Kopec
*Assistant Examiner* — Haidung Nguyen
(74) *Attorney, Agent, or Firm* — Christie, Parker & Hale, LLP

(57) ABSTRACT

A paste composition comprises a dye containing a novel oligomeric compound with improved dispersion performance. The oligomeric compound comprises a tail structure consisting of hydrophilic and hydrophobic blocks and an amine or imidazole head structure. The paste composition can be used to prepare a semiconductor electrode of a solar cell. A semiconductor electrode produced using the paste composition and a solar cell fabricated using the semiconductor electrode exhibit greatly improved power conversion efficiency and superior processability.

8 Claims, 2 Drawing Sheets

PASTE COMPOSITION

CROSS REFERENCE TO RELATED APPLICATIONS

This application is a continuation of U.S. application Ser. No. 11/561,037, filed on Nov. 17, 2006, which claims priority to Korean Patent Application No. 2006-56909, filed on Jun. 23, 2006, and all the benefits accruing therefrom under 35 U.S.C. §119(a), the contents of which are herein incorporated by reference in their entirety.

BACKGROUND OF THE INVENTION

1. Field of the Invention

The present invention relates to a dispersant compound and a method for preparing the same. More specifically, the present invention relates to a novel oligomeric compound with improved dispersion performance, which comprises a tail structure consisting of hydrophilic and hydrophobic blocks and an amine or imidazole head structure, and a method for preparing the oligomeric compound.

2. Description of the Related Art

Dye-sensitized solar cells are photoelectrochemical solar cells that are essentially composed of photosensitive dye molecules capable of absorbing visible light rays to form electron-hole pairs and a transition metal oxide for transferring the generated electrons.

Such dye-sensitized solar cells comprise a semiconductor electrode, an electrolyte, and a counter-electrode wherein the semiconductor electrode consists of a transparent conductive substrate, and a light-absorbing layer including a metal oxide and a dye.

Generally, the semiconductor electrode is produced by forming a metal oxide film on a substrate, and adsorbing a dye on the surface of the metal oxide film. Specifically, the semiconductor electrode is produced by the following procedure. First, a paste composition comprising particles of a metal oxide is applied to a transparent substrate. The paste composition is formed into a metal oxide film by high-temperature annealing at 400-550° C. The metal oxide film is treated with a solution containing a dye for a specified time to adsorb the dye on the available surface of the metal oxide film, thus completing production of the final semiconductor electrode.

According to the general method for producing the semiconductor electrode, since the dye is adsorbed after the metal oxide film is formed on the substrate, the overall surface area of the metal oxide particles is not sufficiently utilized. That is, the area occupied by the dye adsorbed on the metal oxide particles is very small when compared to the optical cross-section of light such that low power conversion efficiency of the solar cells is caused.

When nanoparticles are used to form the metal oxide film, they tend to aggregate within the paste composition. The aggregation of the nanoparticles can lead to a deterioration in uniformity and a low density for the metal oxide film, which in turn can cause low power conversion efficiency in the solar cells.

To address this, many attempts have been made to solve the problems of conventional dye-sensitized solar cells. For example, Korean Patent Laid-open No. 2005-82624 discloses a dye-sensitized solar cell with improved power conversion efficiency, which comprises a semiconductor electrode produced by forming a porous metal oxide film by an electrochemical process using a surfactant, and with a dye adsorbed on the metal oxide film. Further, Japanese Unexamined Patent Publication No. 2002-50413 discloses a dye-sensitized solar cell which comprises an optical semiconductor layer containing porous optical semiconductor particles, wherein the porous optical semiconductor particles are prepared by firing an optical semiconductor powder together with a surfactant or a hydrophilic polymeric compound and dispersion medium at 400° C. or higher, followed by crushing this admixture to form the porous optical semiconductor particles.

According to the conventional dye-sensitized solar cells, however, a surfactant or a dispersant is simply added to a metal oxide powder or optical semiconductor particles and the mixture is formed into a metal oxide film. The introduction of the surfactant advantageously increases the porosity of the metal oxide or the optical semiconductor particles, which in turn allows for the amount of dye that can be adsorbed to be increased and thereby improves the uniformity of the metal oxide film to some extent. However, problems still remain in that since the dye is adsorbed after the metal oxide film or semiconductor layer is formed, the overall surface area of the metal oxide particles is not fully or sufficiently utilized, and as a result, the amount of the dye adsorbed does not substantially or satisfactorily increase and the power conversion efficiency of the solar cells does not therefore improve any further.

There is thus a need to develop a new dispersant that can overcome the above-mentioned problems.

BRIEF SUMMARY OF THE INVENTION

Therefore, the present invention provides, in an embodiment, a novel oligomeric dispersant compound with improved dispersion performance which comprises a tail structure consisting of hydrophilic and hydrophobic blocks and an amine or imidazole head structure.

In another embodiment, a method for preparing the oligomeric dispersant compound is provided.

In another embodiment, a novel dispersant compound is provided, which comprises a tail structure consisting of hydrophilic and hydrophobic blocks, and an amine or imidazole head structure in which the compound is contained as a ligand in a dye having a reactive group such as for example COO⁻ or POO⁻, and which is capable of being bound to the surface of metal oxide particles so that the tail structure functions as a stabilizer to prevent the metal oxide particles from aggregating within a paste composition.

In another embodiment, a paste composition comprises a metal oxide, the oligomeric dispersant compound, a dye, and a binder solution. Sequentially, a metal oxide layer, semiconductor electrode, and solar cell can be formed from the paste composition.

BRIEF DESCRIPTION OF THE DRAWINGS

The above and other features and advantages of the present invention will be more clearly understood from the following detailed description taken in conjunction with the accompanying drawings, in which.

DETAILED DESCRIPTION OF THE INVENTION

Figure 1:
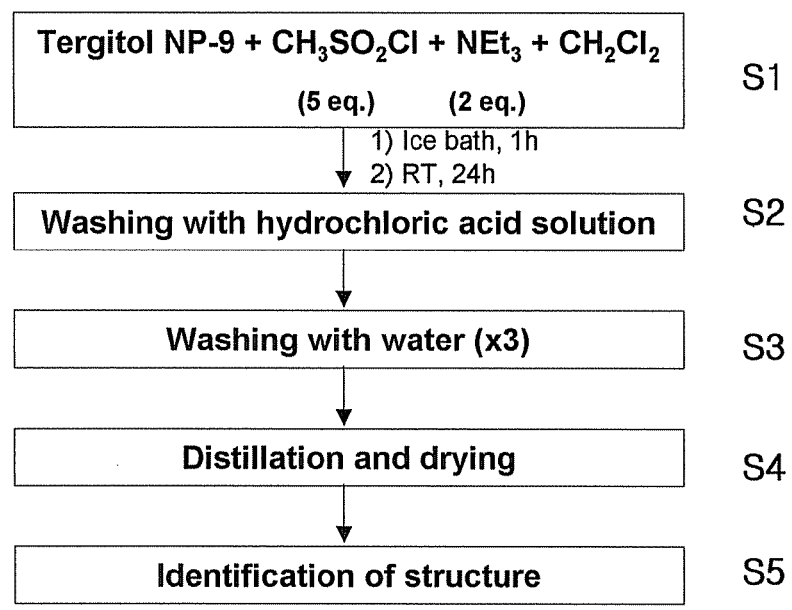
FIG. 1 is a process chart schematically showing exemplary production of a Tergitol-mesylate as an intermediate of a dispersant compound, which is prepared in step (1) of Synthesis Example 1.

The present invention will now be described in greater detail.

It will be understood in the following disclosure of the present invention, that as used herein, the term "and/or" includes any and all combinations of one or more of the associated listed items. In addition, the singular forms "a", "an" and "the" are intended to include the plural forms as well, unless the context clearly indicates otherwise. It will be further understood that the terms "comprise", "comprises", and "comprising," when used in this specification, specify the presence of stated features, integers, steps, operations, elements, components, and/or combination of the foregoing, but do not preclude the presence and/or addition of one or more other features, integers, steps, operations, elements, components, groups, and/or combination of the foregoing. The use of the terms "first", "second", and the like, where included, are for purposes of distinguishing elements only, and therefore should not be considered as implying any particular order or sequence unless otherwise specified.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The present invention provides a compound represented by Formula 1 below:

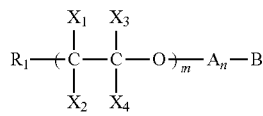
(1)

wherein $R_1$ is an amine or imidazole group, $X_1$, $X_2$, $X_3$ and $X_4$ are each independently H or methyl, A is a substituted or unsubstituted $C_6$-$C_{30}$ arylene group, a substituted or unsubstituted $C_6$-$C_{30}$ arylalkylene group, or a substituted or unsubstituted $C_6$-$C_{30}$ cycloalkylene group, B is a substituted or unsubstituted $C_1$-$C_{20}$ alkyl group, a substituted or unsubstituted $C_1$-$C_{20}$ alkenyl group, or a substituted or unsubstituted $C_1$-$C_{20}$ alkynyl group, wherein B may have a linear or branched structure, m is an integer from 1 to 20, and n is 0 or 1.

That is, the compound of Formula 1 according to the present invention comprises four moieties, i.e. an amine moiety, a polyethylene glycol ("PEG") moiety, a cyclic moiety, and an aliphatic hydrocarbon moiety, along the molecular chain of the compound.

Of these moieties, the cyclic moiety (corresponding to 'A' in Formula 1) may be a substituted or unsubstituted $C_6$-$C_{30}$ arylene group, a substituted or unsubstituted $C_6$-$C_{30}$ arylalkylene group, or a substituted or unsubstituted $C_6$-$C_{30}$ cycloalkylene group. The aliphatic hydrocarbon moiety (corresponding to 'B' in Formula 1) may be a substituted or unsubstituted alkyl group, a substituted or $C_1$-$C_{20}$ unsubstituted $C_1$-$C_{20}$ alkenyl group, or a substituted or unsubstituted $C_1$-$C_{20}$ alkynyl group, which may exist in a linear or branched form.

Specific examples of the alkyl group include linear or branched alkyl groups, such as methyl, ethyl, propyl, isobutyl, sec-butyl, tert-butyl, pentyl, iso-amyl and hexyl, but is not limited to these. At least one hydrogen atom contained in the alkyl group may be substituted with a halogen atom, a hydroxyl group, a nitro group, a cyano group, an amino group, an amidino group, a hydrazine group, a hydrozone group, or the like.

The term "alkenyl" or "alkynyl" as used herein refers to a group that contains at least one carbon-carbon double or triple bond at an intermediate or terminal position of the alkyl group defined above. At least one hydrogen atom contained in the alkenyl or alkynyl group may be substituted with the same substituent as defined with respect to the alkyl group.

The term "arylene" as used herein refers to a carbocyclic aromatic system including one or more aromatic rings in which the rings may be attached together in a pendant manner or may be fused. Specific examples of the arylene group include aromatic groups, such as phenyl, naphthyl, and tetrahydronaphthyl. At least one hydrogen atom contained in the arylene group may be substituted with the same substituent as defined with respect to the alkyl group.

The term "arylalkylene" as used herein refers to a group in which a part of hydrogen atoms contained in the arylene group defined above are substituted with lower alkyl radicals, such as methylene, ethylene and propylene. Examples of the arylalkylene group include benzylene and phenylethylene. At least one hydrogen atom contained in the arylalkylene group may be substituted with the same substituent as defined with respect to the alkyl group.

The term "cycloalkylene" as used herein refers to a $C_6$-$C_{30}$ monovalent monocyclic system. At least one hydrogen atom contained in the cycloalkylene group may be substituted with the same substituent as defined with respect to the alkyl group.

in an embodiment, the average number (m) of the repeating units in the polyethylene glycol moiety is 5 to 10. In another embodiment, the aliphatic hydrocarbon moiety is a branched form having greater than or equal to 5 carbon atoms. As the length of the polyethylene glycol moiety decreases, the adsorption of the compound of Formula 1 to particles increases. As the aliphatic hydrocarbon moiety has a long chain and is bulky, it can maintain constant spacing interval between particles, which in turn can mitigate or reduce the agglomeration of particles and thus improve the stability of the particles toward agglomeration.

Specific examples of compounds that can be represented by Formula 1 include compounds represented by Formulae 2 and 3 below:

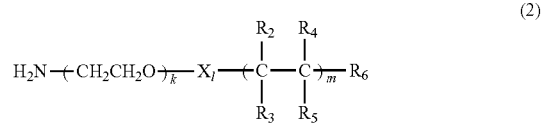
(2)

wherein X is

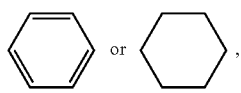

$R_2$, $R_3$, $R_4$, $R_5$ and $R_6$ are each independently H or methyl,
k is an integer from 5 to 10,
l is 0 or 1, and
m is an integer from 4 to 10; and

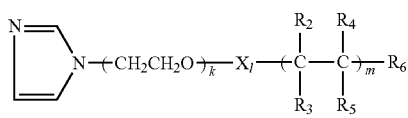
(3)

wherein X, $R_2$, $R_3$, $R_4$, $R_5$, $R_6$, k, l and m are as defined in Formula 2.

More specifically, the compound of Formula 1 according to the present invention may be a compound represented by Formula 4 or 5 below:

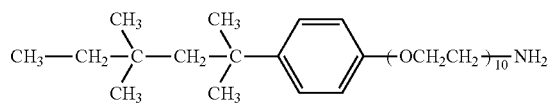
(4)

(5)

The compound of Formula 1 according to the present invention may be synthesized by the following reaction scheme 1 below:

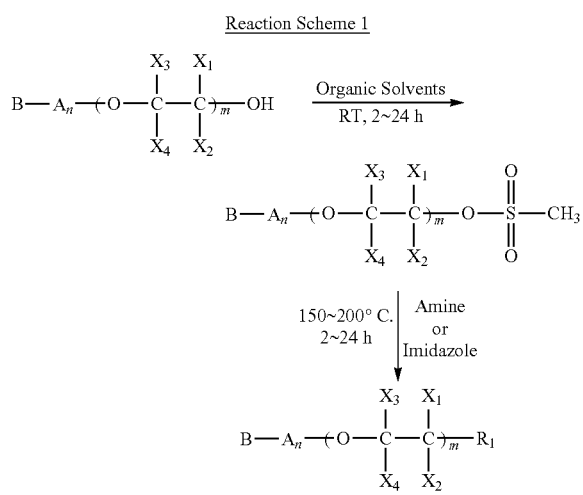

wherein
$R_1$, $X_1$, $X_2$, $X_3$, $X_4$, A, B, m and n are as defined in Formula 1.

Specifically, the dispersant compound of Formula 1 may be synthesized by a method comprising the following steps:

(1) adding organic solvents to a compound of Formula 6 below:

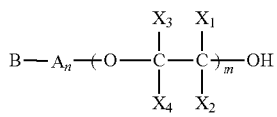
(6)

wherein $X_1$, $X_2$, $X_3$, $X_4$, A, B, m and n are as defined in Formula 1, and reacting the compound of Formula 6 with methanesulfonyl chloride for a specified time to prepare a compound represented by Formula 7 below:

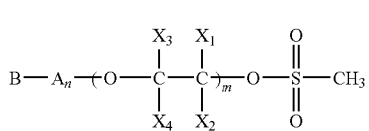
(7)

wherein $X_1$, $X_2$, $X_3$, $X_4$, A, B, m and n are as defined in Formula 1; and (2) adding an amine or imidazole compound to the compound of Formula 7, and allowing the mixture to react for a specified time to prepare the compound of Formula 1.

More specifically, the compound of Formula 1 according to the present invention may be synthesized in accordance with the following procedure. An organic solvent is added to the compound of Formula 6. The compound of Formula 6 is allowed to react with methanesulfonyl chloride for a specified time. The organic solvent is removed, and the resulting residue is dried to prepare an intermediate (Formula 7) having a methanesulfonyl group. After an amine or imidazole compound is added to the intermediate of Formula 7 in an organic solvent, the mixture is allowed to react for a specified time. The organic solvent is removed, and the resulting residue is filtered, purified and dried to prepare the final compound of Formula 1.

Non-limiting examples of suitable organic solvents that can be used in the reactions include: aliphatic hydrocarbon solvents, such as hexane and heptane; aromatic hydrocarbon solvents, such as toluene, pyridine, quinoline, anisole, mesitylene, and xylene; ketone-based solvents, such as methyl isobutyl ketone, N-methyl-2-pyrrolidone ("NMP"), 1-methyl-2-pyrrolidinone, cyclohexanone, and acetone; ether-based solvents, such as dimethoxy ether, tetrahydrofuran and isopropyl ether; alcohol-based solvents, such as ethanol ("EtOH"), isopropyl alcohol, butyl alcohol and t-butyl alcohol; amide-based solvents, such as dimethylacetamide and dimethylformamide ("DMF"); silicon-based solvents; nitrile-based solvents, such as acetonitrile; methanesulfonyl chloride; dichloromethane ($CH_2Cl_2$); triethylamine ($NEt_3$); and mixtures thereof.

The reaction of step (1) is carried out under a nitrogen atmosphere at room temperature for 2-4 hours, and the reaction of step (2) is carried out at 150-200° C. for 2-24 hours, more specifically for 10-14 hours.

The washing, distillation and drying steps may be subsequently carried out after step (2). The subsequent steps may be carried out without limitation by conventional methods.

The dispersant compound comprises a tail structure consisting of hydrophilic and hydrophobic blocks and an amine or imidazole head structure. Based on this structure, the dispersant compound functions to prevent aggregation of metal oxide particles within a paste to improve the uniformity of the metal oxide particles and to increase the density of a film formed of the paste.

The dispersant compound is included as a ligand with a dye, to thereby constitute a tail part of the dye. That is, the dye containing the dispersant compound includes the dispersant compound as a functional group which acts as a dispersant. Accordingly, the dye containing the dispersant compound performs the following two functions: (1) the dye containing the dispersant compound is adsorbed on the surface of metal oxide particles to transfer electrons exited by absorbed light to a conduction band of the metal oxide; and (2) the dye containing the dispersant compound itself functions as a dispersant to prevent aggregation of the metal oxide particles, thereby improving the uniformity of the particles within a paste and increasing the density of a film formed of the paste. The dye containing the dispersant compound can be used to prepare a paste composition for a semiconductor electrode of a solar cell. A semiconductor electrode produced using the paste composition and a solar cell fabricated using the semiconductor electrode exhibit improved power conversion efficiency and superior processability.

Exemplary dyes that may be combined with the dispersant compound include ruthenium complexes such as ruthenium trisbipyridyl; xanthene colorants, including Rhodamine B, Rose Bengal, eosin, and erythrosine; cyanine colorants, including quinocyanine and cryptocyanine; basic dyes; phenosafranine, Capri blue, thiosine, and Methylene Blue; porphyrinoid compounds, including chlorophyll, zinc porphyrin, and magnesium porphyrin; azo colorants; phthalocyanine compounds; anthraquinone colorants; polycyclic quinone colorants; and mixtures thereof. These dyes may be used alone or in combinations comprising two or more of the dyes. Any dye material that can be generally used in the field of solar cells may be used without any limitation. In an embodiment, Gräzel-type dyes, such as ruthenium compounds (e.g., N3, N719, Black Dye, and the like), are specifically useful.

The present invention also provides a paste composition for the formation of a semiconductor electrode which comprises a dye containing the compound of Formula 1.

Specifically, the paste composition comprises a dye, a binder solution for low-temperature annealing and a metal oxide powder wherein the dye contains the compound of Formula 1.

In a conventional method for producing a semiconductor electrode of a dye-sensitized solar cell, the dye is adsorbed after a metal oxide film is formed on a substrate, and therefore the overall surface area of metal oxide particles is not sufficiently utilized. The area actually occupied by the dye adsorbed on the metal oxide particles is generally only a tenth of the optical cross-section of light.

According to the paste composition of present invention, the dye containing the dispersant compound, acting as a dispersant, is added to a slurry dispersion to increase the amount of the dye adsorbed over the entire surface of the metal oxide particles, as well as to improve the dispersibility and uniformity of the metal oxide particles. As a result, a semiconductor electrode and a solar cell using the paste composition exhibit superior processability and improved power conversion efficiency.

On the other hand, the paste composition uses a binder that can be easily removed by low-temperature annealing. One example of the binder for low-temperature annealing is t-butanol. Since t-butanol has a melting point of 25-26° C. and a boiling point of 80° C., it is completely removed even by low-temperature annealing at 350° C. and exists in a solid state at 25° C. or lower. Based on these characteristics, t-butanol serves to provide strong binding effects due to its hydrogen bonding to the paste composition after drying.

Therefore, conventional paste compositions which use binders that can be removed only by high-temperature annealing at 350° C. or higher can have poor applicability to flexible plastic substrates. In contrast, since the paste composition disclosed herein uses a binder for low-temperature annealing, e.g., t-butanol, in view of the aforementioned characteristics, the paste composition disclosed herein can be advantageously applied to flexible substrates, including plastic substrates.

The paste composition, as disclosed herein, comprises 20 to 50% by weight of the metal oxide powder, 0.1 to 10% by weight of the dye containing the compound of Formula 1 with respect to the weight of the metal oxide powder, and the balance of the paste composition comprises the binder solution.

When the dye containing the compound of Formula 1 is used in an amount of less than 0.1% by weight, relative to the weight of the metal oxide powder, the desirable properties (for example, an increase in the amount of the dye adsorbed on the metal oxide powder, sufficient injection of electrons excited by absorbed light into a conduction band of the metal oxide, and desired dispersion effects of the dye) cannot be attained. Meanwhile, when the dye containing the compound of Formula 1 is used in an amount exceeding 10% by weight, relative to the weight of the metal oxide powder, the excess dye that remains unadsorbed to the metal oxide (e.g., $TiO_2$) may cause electrochemical side reactions, which can result in decreased power conversion efficiency.

In an embodiment, the binder solution for low-temperature annealing is prepared by mixing a solvent and t-butanol in a weight ratio (w/w) of 1:1 to 1:10. If t-butanol and the solvent are mixed in a weight ratio of less than 1:1 (i.e. the amount of the solvent is relatively large, compared to that of the t-butanol), the viscosity of the paste composition is reduced. Low viscosity of the paste composition can cause poor adhesiveness, for example, leading to degradation in the quality of a semiconductor electrode produced using the paste composition. If the solvent and t-butanol are mixed in a weight ratio of greater than 1:10 (i.e. where the amount of the solvent is relatively small when compared to that of the t-butanol), the initial viscosity of the paste composition is high. High initial viscosity reduces the amount of $TiO_2$ loaded, making it impossible to produce a semiconductor electrode having the intended quality and desired physical properties.

A general organic solvent or water can be used as the solvent of the binder solution. PA solvent that is more polar and has a higher hydrogen bond index than t-butanol is desirable. Examples of such solvents include water, glycols, and glycerols. In an embodiment, an aqueous solvent is used.

The presence of increasing amounts of hydroxyl ("OH") groups in the paste composition, such as those provided by the solvent, increases the viscosity of the paste composition, making coating of the composition difficult. For better coatability of the composition, an acetate-based solvent selected from ethyl acetate, butyl acetate, propylene glycol methyl ether acetate, propylene glycol mono ether acetate ("PGMEA") and dihydroterpineol acetate ("DHTA") may be added to the paste composition.

The paste composition comprises at least one metal oxide selected from the group consisting of titanium, niobium, hafnium, indium, tin, and zinc oxides. The metal oxide may be used alone or in a combination comprising at least one of the foregoing metal oxides. In an exemplary embodiment, titanium oxide ($TiO_2$) is a useful metal oxide.

The metal oxide desirably has a large surface area so that the dye adsorbed on the surface of the metal oxide can absorb as much light as possible, and the degree of adsorption to an electrolyte layer can be increased. In an embodiment, the metal oxide can have a nanostructure selected from nanotubes, nanowires, nanobelts, and nanoparticles. In a specific embodiment, the particle diameter of the metal oxide is preferably within 5 nm and 400 nm.

Further, as disclosed herein, a semiconductor electrode is produced using the paste composition.

Specifically, the semiconductor electrode comprises a transparent electrode composed of a substrate and an electrically conductive material coated on the substrate, a metal oxide layer formed on the transparent electrode on the side of the transparent electrode having the electrically conducting material, and a dye present in the metal oxide layer, wherein the dye contains the dispersant compound of Formula 1.

The substrate may be of any type as long as it is transparent. Examples of substrates include glass substrates, silica substrates, and plastic substrates.

Electrically conductive material for coating on the substrate include, for example, indium tin oxide ("ITO"), fluorine-doped tin oxide ("FTO"), $ZnO$—$Ga_2O_3$, $ZnO$—$Al_2O_3$, or $SnO_2$—$Sb_2O_3$.

The semiconductor electrode is produced by a method comprising applying the paste composition to a transparent substrate coated with an electrically conductive material, and low-temperature annealing the coated composition at a temperature of 80 to 200° C. for 0.5-5 hours, to form a light-absorbing layer.

The use of the paste composition, which comprises the dye containing the compound of Formula 1 and the metal oxide, in the production of the semiconductor electrode avoids the need to separately perform the steps of forming a metal oxide layer and adsorbing a dye on the surface of the metal oxide layer in accordance with conventional methods for the production of a transparent electrode. In addition, the use of t-butanol having a boiling point of 80° C. as a binder in the method of the present invention enables the formation of a light-absorbing layer through low-temperature annealing at 80-200° C. Accordingly, the method of the present invention is economically advantageous in terms of production cost and processing.

Furthermore, since the low-temperature annealing permits the method to be applied to flexible substrates (e.g., plastic substrates) without any particular difficulty, the method disclosed herein is advantageous for a wide range of applications.

The application of the paste composition may be carried out by a general coating technique, for example, spraying, spin coating, dipping, printing, doctor blading, sputtering, chemical deposition, physical deposition, or electrophoresis. The coating of the electrically conductive material may be carried out by a general coating technique.

The coated composition is subjected to low-temperature annealing at 80-200° C. for 0.5-5 hours and preferably 90-150° C. for 1-3 hours to form a light-absorbing layer.

The surface shape of the light-absorbing layer may be planar or irregular. The light-absorbing layer preferably has an irregular surface shape so that it can be sufficiently adsorbed to an electrolyte layer. Suitable irregular surface shapes of the light-absorbing layer include steps, needles, meshes, scars, and other shapes, but are not limited thereto.

The light-absorbing layer may be formed into a monolayer or a bilayer structure. The bilayer structure of the light-absorbing layer can be formed using two paste compositions which comprise different metal oxides having different particle sizes in order to improve the transmittance of light incident on the light-absorbing layer. In an embodiment, a bilayer structure of the light-absorbing layer consists of a 10-20 μm thick layer formed of a metal oxide with a particle size of 9-20 nm and a 3-5 μm thick layer formed of a metal oxide with a particle size of 200-400 nm.

The semiconductor electrode thus has excellent processability, the amount of the dye adsorbed to the metal oxide is greater than can be obtained using conventional methods, and the physical properties of the metal oxide film are uniform. Therefore, the semiconductor electrode of the present invention can be used to fabricate dye-sensitized solar cells with improved power conversion efficiency.

The present invention also provides a dye-sensitized solar cell comprising the semiconductor electrode, an electrolyte layer, and a counter electrode.

The electrolyte layer is composed of an electrolyte solution, for example, a solution of iodine in acetonitrile, an NMP solution, or a 3-methoxypropionitrile solution. Any electrolyte solution may be used, without limitation, so long as it exhibits hole conductivity.

The counter electrode can be made of, without any limitation, an electrically conductive material. As long as a conductive layer is disposed on the surface of the counter electrode facing the semiconductor electrode, any suitable insulating material may be used to form the counter electrode. In an embodiment, an electrochemically stable material is used to form the counter electrode. Specific examples of electrochemically stable materials include platinum, gold, and carbon. For the purpose of improving the catalytic effects of oxidation and reduction, the surface of the counter electrode facing the semiconductor electrode can have a microstructure with increased surface area. In an exemplary embodiment, the counter electrode is made of platinum black or porous carbon. A platinum black counter electrode can be produced by anodic oxidation of platinum, by treatment of platinum with hexachloroplatinate, and the like. The porous carbon counter electrode can be produced by sintering of fine carbon particles or by baking of an organic polymer.

The dye-sensitized solar cell of the present invention can be fabricated by any suitable method including known methods.

Hereinafter, the present invention will be explained in more detail with reference to the following examples. These examples are provided for the purpose of illustration and are not to be construed as limiting the scope of the invention.

EXAMPLES

Synthesis Example 1

Synthesis of Oligomeric Compound

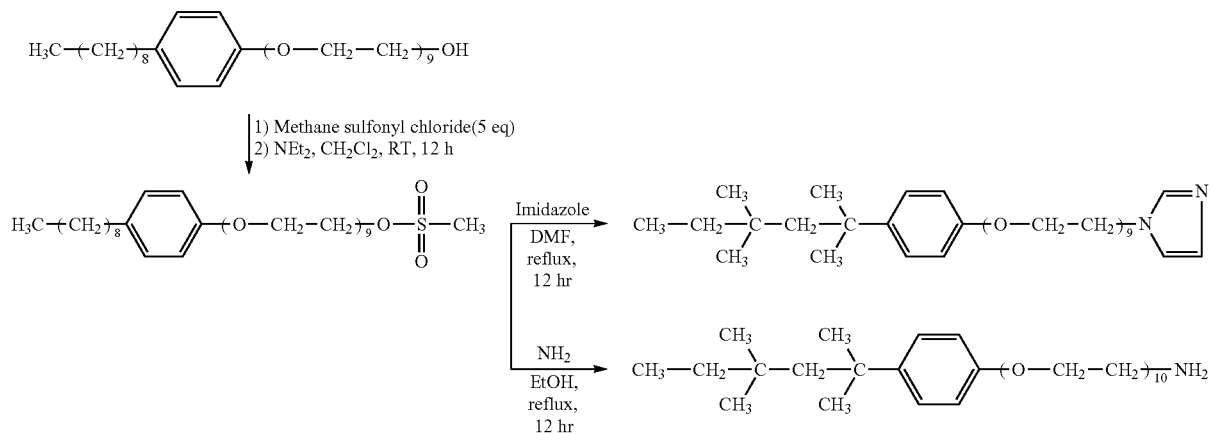

Reaction Scheme 2

(1) Synthesis of Tergitol-Mesylate

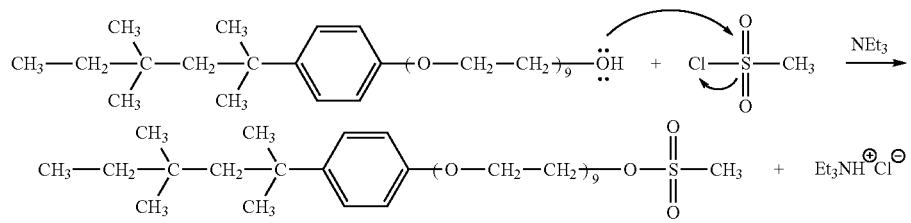

Reaction Scheme 3

The Tergitol-mesylate was synthesized as depicted in Reaction Scheme 3 and FIG. 1. In step S1, 4.86 g (48 mmol) of triethylamine (Aldrich) was added to a solution of Tergitol®NP-9 (16 mmol, Aldrich) in anhydrous methylene chloride (20 ml) in a reactor. The mixture was stirred under a nitrogen atmosphere for 10 minutes.

Also in step S1, after the reactor was placed in an ice bath, the mixture was allowed to react while adding 5.5 g (48 mmol) of methanesulfonyl chloride (Aldrich) portionwise to the mixture over one hour. Thereafter, the reactor was slowly allowed to warm to room temperature with stirring over 12 hours.

After completion of the reaction, the reaction mixture was poured into cold water, followed by phase separation. The obtained organic layer was sequentially washed with a hydrochloric acid solution (×1, step S2) and water (×3, step S3). The solvents were removed from the methylene chloride solution using a rotary evaporator to obtain a viscous liquid (step S4). The liquid was dried in a vacuum oven to give the Tergitol-mesylate (step S4).

Figure 2:
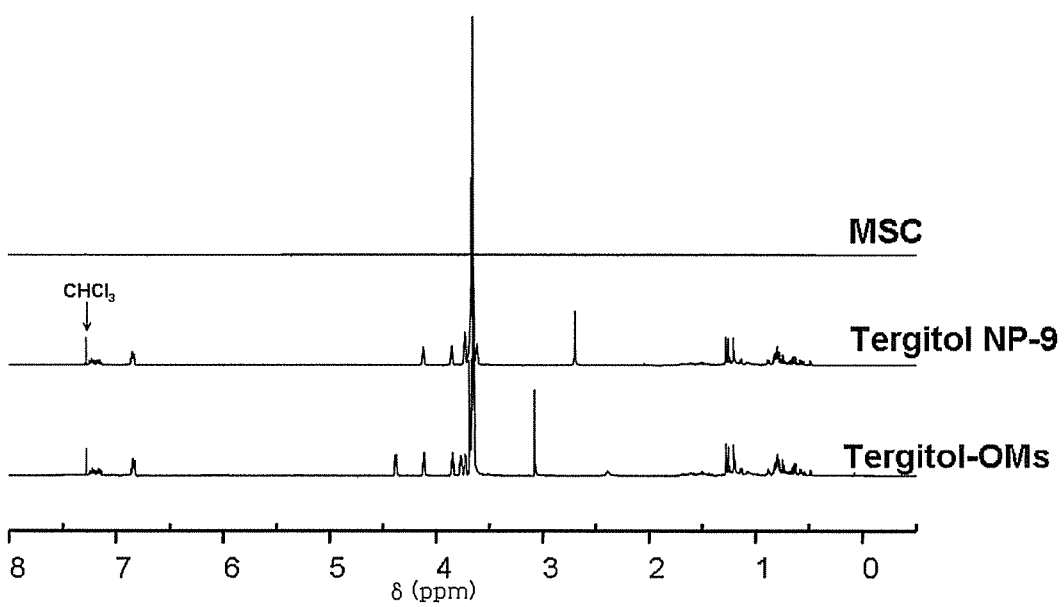
FIG. 2 shows $^1$H-NMR spectra identifying the structure of a Tergitol-mesylate as an exemplary intermediate of a dispersant compound of the present invention, which is prepared in step (1) of Synthesis Example 1.

The structure of the product was identified by $^1$H-NMR spectroscopy (step S5 in FIG. 1; $^1$H-NMR spectrum of Tergitol-mesylate shown in FIG. 2).

(2) Synthesis of Tergitol-Amine 0.44 g (0.64 mmol) of the Tergitol-mesylate prepared in (1) was dissolved in 20 ml of ethanol. The solution was stirred at room temperature for 15 minutes. 0.065 g (0.64 mmol) of ammonia (Aldrich) was added to the solution and refluxed with stirring at 160° C. for 12 hours.

After completion of the reaction, the reaction mixture was poured into an excess of cold water, and extracted with methylene chloride. The obtained organic layer was washed with a hydrochloric acid solution.

The solvents were removed from the methylene chloride solution using a rotary evaporator to obtain a viscous liquid. The liquid was dried in a vacuum oven to give the Tergitol-amine.

Figure 3:
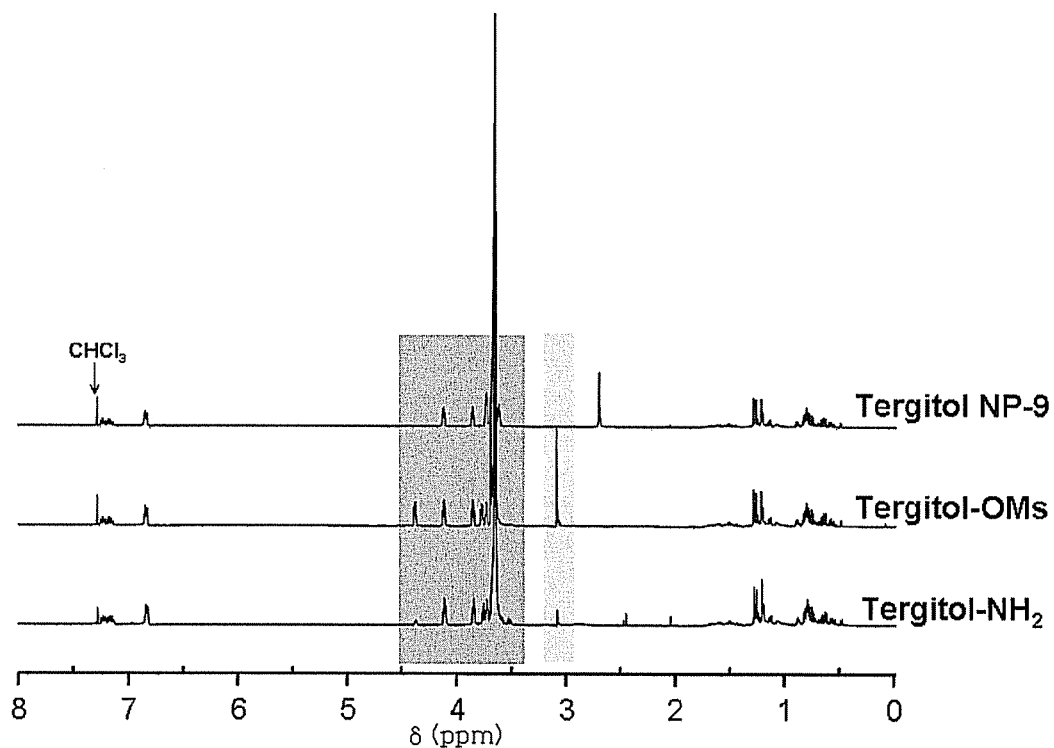
FIG. 3 shows $^1$H-NMR spectra identifying the structure of a Tergitol-amine prepared in step (2) of Synthesis Example 1.

The structure of the product was identified by $^1$H-NMR spectroscopy (FIG. 3). The $^1$H-NMR analysis shows that peaks corresponding to the ethylene oxide (—CH$_2$CH$_2$O—) were shifted and a peak at around 3 ppm corresponding to the mesylate disappeared, indicating the introduction of the amine group in a yield of 80%.

(3) Synthesis of Tergitol-Imidazole 0.44 g (0.65 mmol) of the Tergitol-mesylate prepared in (1) was dissolved in 20 ml of ethanol. The solution was stirred at room temperature for 15 minutes. 0.394 g (0.64 mmol) of imidazole (2.0 M in dimethylformamide, Aldrich) was added to the solution and refluxed with stirring at 160° C. for 12 hours.

After completion of the reaction, the reaction mixture was poured into an excess of cold water, and extracted with methylene chloride. The obtained organic layer was washed with a hydrochloric acid solution.

The solvents were removed from the methylene chloride solution using a rotary evaporator to obtain a viscous liquid. The liquid was dried in a vacuum oven to give the Tergitol-imidazole.

Figure 4:
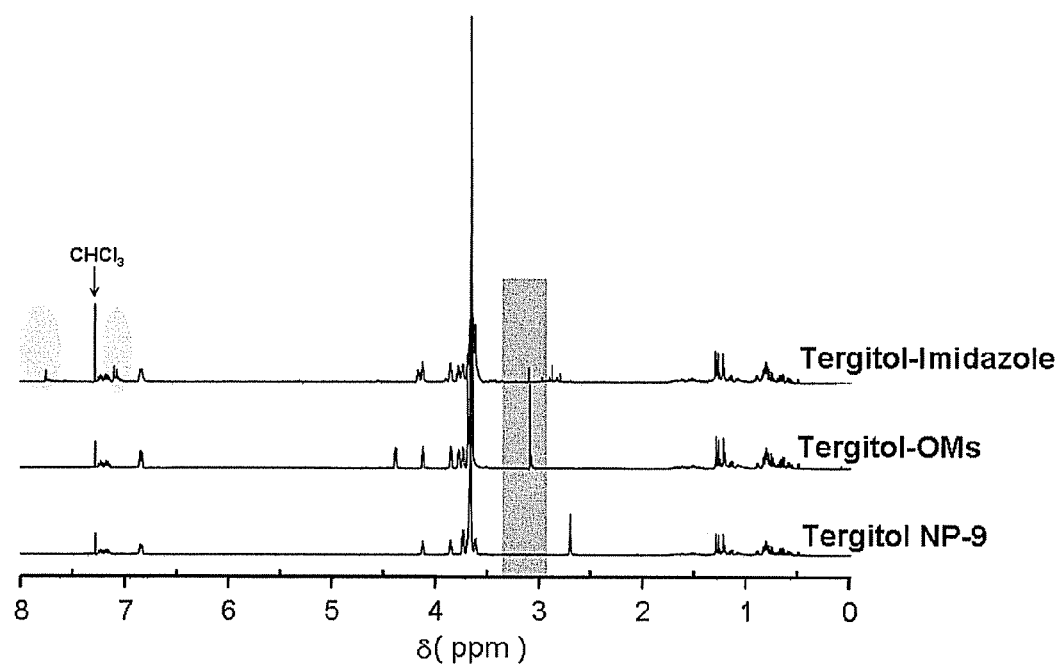
FIG. 4 shows $^1$H-NMR spectra identifying the structure of an exemplary Tergitol-imidazole prepared in step (3) of Synthesis Example 1.

The structure of the product was identified by $^1$H-NMR spectroscopy (FIG. 4). The $^1$H-NMR analysis shows that new peaks of the aromatic compound appeared at 7-8 ppm and a peak at around 3 ppm corresponding to the mesylate disappeared, indicating the introduction of the imidazole group in a yield of 100%.

Synthesis Example 2

Synthesis of Ruthenium Dye Containing Tergitol-Amine 70 mg (0.094 mmol) of ruthenium 535 (N3 dye, Solaronix) and 394 mg (0.64 mmol) of the Tergitol-amine were dissolved in 10 ml of ethanol and stirred at room temperature for one hour.

The solvent was removed from the reaction solution using a rotary evaporator to obtain a viscous liquid. The liquid was dissolved in a small amount of methylene chloride, and poured into n-hexane to obtain a precipitate. The precipitate was dried in a vacuum oven to give a ruthenium dye containing the Tergitol-amine.

Synthesis Example 3

Synthesis of Ruthenium Dye Containing Tergitol-Imidazole)

A ruthenium dye containing the Tergitol-imidazole was prepared in the same manner as in Synthesis Example 2, except that 425 mg (0.64 mmol) of the Tergitol-imidazole was used instead of the Tergitol-amine.

Preparative Example 1

Preparation of Paste Composition)

Water and t-butanol were mixed in a weight ratio of 1:2 (w/w) to prepare a binder solution. 7 g of the binder solution was mixed with 120 mg of the dye prepared in Synthesis Example 2 and stirred for 30 minutes. To the mixture was added 3 g of a $TiO_2$ powder (particle diameter: 13 nm), followed by stirring for one hour to prepare a paste composition.

Example 1

Production of Semiconductor Electrode and Fabrication of Solar Cell (1)

(1) Production of Semiconductor Electrode

Fluorine-doped tin oxide (FTO) was applied to a glass substrate using a sputter coater. The paste composition prepared in Preparative Example 1 was applied to the resulting substrate by screen printing and annealed at 120° C. for one hour to form a light-absorbing layer having a thickness of about 20 μm, completing the production of a semiconductor electrode.

(2) Fabrication of Solar Cell

Platinum was coated on the surface of an ITO-coated transparent conductive glass substrate to form a counter electrode. The counter electrode (i.e. positive electrode) and the semiconductor electrode (i.e. negative electrode) produced in Example 1 were assembled. At this time, both electrodes were arranged in such a manner that the conducting surfaces of the electrodes faced to each other. After a polymer film (SURLYN®, DuPont) having a thickness of about 40 μm was interposed between the two electrodes, the two electrodes were adhered to each other under a pressure of 1 to 2 atm (0.1 to 0.2 MPa) on a hot plate at 100-140° C. An electrolyte solution was filled in a space formed between the two electrodes through a fine hole penetrating the positive electrode to complete fabrication of a dye-sensitized solar cell. As the electrolyte solution, an $I_3^-/I^-$ electrolyte solution of 0.6 moles of 1,2-dimethyl-3-octyl-imidazolium iodide, 0.2 moles of LiI, 0.04 moles of $I_2$ and 0.2 moles of 4-tert-butylpyridine ("TBP") in acetonitrile was used.

Example 2

Production of Semiconductor Electrode and Fabrication of Solar Cell (2)

A semiconductor electrode was produced in the same manner as in Example 1, except that a $TiO_2$ layer having a thickness of 17.720 μm was used as the metal oxide layer. A dye-sensitized solar cell was fabricated using the semiconductor electrode by the procedure of Example 1.

Comparative Example 1

Production of Semiconductor Electrode and Fabrication of Solar Cell

A semiconductor electrode was produced in the same manner as in Example 1, except that ruthenium 535 (N3 dye) was used as the dye and a $TiO_2$ layer having a thickness of 16.600 μm was used as the metal oxide layer. A dye-sensitized solar cell was fabricated using the semiconductor electrode by the procedure of Example 1.

Comparative Example 2

Production of Semiconductor Electrode and Fabrication of Solar Cell

A semiconductor electrode was produced in the same manner as in Comparative Example 1, except that a $TiO_2$ layer having a thickness of 17.288 μm was used as the metal oxide layer. A dye-sensitized solar cell was fabricated using the semiconductor electrode by the procedure of Example 1.

Comparative Example 3

Production of Semiconductor Electrode and Fabrication of Solar Cell

A semiconductor electrode was produced in the same manner as in Example 1, except that N719 was used as the dye and a $TiO_2$ layer having a thickness of 16.559 μm was used as the metal oxide layer. A dye-sensitized solar cell was fabricated using the semiconductor electrode by the procedure of Example 1.

Comparative Example 4

Production of Semiconductor Electrode and Fabrication of Solar Cell

A semiconductor electrode was produced in the same manner as in Comparative Example 3, except that a $TiO_2$ layer having a thickness of 17.258 μm was used as the metal oxide layer. A dye-sensitized solar cell was fabricated using the semiconductor electrode by the procedure of Example 1.

Test Example 1

Evaluation of Power Conversion Efficiency of Solar Cells

The photovoltages and photocurrents of the solar cells fabricated in Examples 1 and 2 and Comparative Examples 1 to 4 were measured to calculate the power conversion efficiency of the solar cells. For the measurements, a xenon lamp (01193, Oriel) was used as a light source, and a standard solar cell (Frunhofer Institute Solar Engeriessysteme, Certificate No. C—ISE369, Type of material: Mono-$Si^+$ KG filter) was used to compensate for the solar conditions (AM 1.5) of the xenon lamp.

The photocurrent density ("$I_{sc}$"), open-circuit voltage ("$V_{oc}$") and fill factor ("FF") of the solar cells were determined from the obtained respective photocurrent-photovoltage curves, and the power conversion efficiency ($\eta_e$) of the solar cells was calculated according to the following equation:

$$\eta_e (\%) = (V_{oc} \cdot I_{sc} \cdot FF)/(P_{inc}) \times 100$$

where $P_{inc}$ is 100 mw/cm² (1 sun).

The obtained results are shown in Table 1. The thicknesses of the $TiO_2$ layers used in the dye-sensitized solar cells are shown in Table 1.

TABLE 1

| Example No. | $J_{sc}$ (mA/cm²) | $V_{oc}$ (mV) | FF | $\eta_e$ (%) | Thickness of $TiO_2$ layer (μm) |
|---|---|---|---|---|---|
| Example 1 | 10.572 | 640.922 | 0.738 | 5.023 | 16.739 |
| Example 2 | 10.546 | 620.904 | 0.713 | 4.688 | 17.720 |
| Comparative Example 1 | 8.773 | 589.706 | 0.699 | 3.631 | 16.600 |
| Comparative Example 2 | 9.787 | 603.938 | 0.745 | 4.421 | 17.288 |
| Comparative Example 3 | 9.333 | 637.220 | 0.762 | 4.548 | 16.559 |
| Comparative Example 4 | 9.212 | 596.140 | 0.700 | 3.861 | 17.258 |

As can be seen from the results of Table 1, the solar cells in which the Tergitol dispersant having a high affinity for $TiO_2$ was introduced into the metal oxide layer with the metal oxide particles and ruthenium dye, showed high power conversion efficiency.

Although the preferred embodiments of the present invention have been disclosed for illustrative purposes, those skilled in the art will appreciate that various modifications and variations are possible, without departing from the scope and spirit of the invention as disclosed in the appended claims. Accordingly, such modifications and variations are intended to come within the scope of the appended claims.

As apparent from the above description, the dispersant compound is contained as a ligand in a dye to constitute a tail part of the dye. That is, the dye containing the dispersant compound has a functional group acting as a dispersant. Accordingly, the dye containing the dispersant compound performs the following two functions: (1) the dye is adsorbed on the surface of metal oxide particles to transfer electrons excited by absorbed light to a conduction band of the metal oxide; and (2) the dye functions as a dispersant to prevent aggregation of the metal oxide particles, thereby improving the uniformity of the particles within a paste and increasing the density of a film formed of the paste. The dye containing the dispersant compound can be used to prepare a paste composition for a semiconductor electrode of a solar cell. A semiconductor electrode produced using the paste composition and a solar cell fabricated using the semiconductor electrode exhibit greatly improved power conversion efficiency and superior processability.

What is claimed is:

1. A paste composition comprising
a metal oxide powder;
a dye containing a compound represented by Formula 1 below:

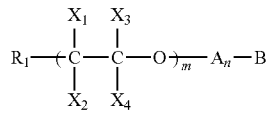

wherein $R_1$ is an amine group,
$X_1$, $X_2$, $X_3$ and $X_4$ are each independently H or methyl,
A is a substituted or unsubstituted $C_6$-$C_{30}$ arylene group, a substituted or unsubstituted $C_6$-$C_{30}$ arylalkylene group, or a substituted or unsubstituted $C_6$-$C_{30}$ cycloalkylene group,
B is a substituted or unsubstituted $C_1$-$C_{20}$ alkyl group, a substituted or unsubstituted $C_2$-$C_{20}$ alkenyl group, or a substituted or unsubstituted $C_3$-$C_{20}$ alkynyl group, wherein B has a linear or branched structure,
m is an integer from 1 to 20, and
n is 0 or 1; and
a binder solution.

2. The paste composition of claim 1, comprising
20 to 50% by weight of the metal oxide powder;
0.1 to 10% by weight of the dye containing the compound of Formula 1 with respect to the weight of the metal oxide powder; and
wherein the balance of the paste composition comprises the binder solution.

3. The paste composition of claim 1, wherein the dye further comprises ruthenium complexes; xanthene colorants; cyanine colorants; basic dyes; phenosafranine; Capri blue; thiosine; Methylene Blue; porphyrinoid compounds; azo colorants; phthalocyanine compounds; anthraquinone colorants; polycyclic quinone colorants; or a combination comprising two or more of the foregoing dyes.

4. The paste composition of claim 1, wherein the dye further comprises ruthenium trisbipyridyl, Rhodamine B, Rose Bengal, eosin, erythrosine, quinocyanine cryptocyanine, chlorophyll, zinc porphyrin, magnesium porphyrin, or mixtures thereof.

5. The paste composition of claim 1, wherein the binder composition comprises a solvent and t-butanol in a weight ratio (w/w) of 1:1 to 1:10.

6. The paste composition of claim 5, wherein the solvent comprises water, glycols, glycerols, or an acetate-based solvent.

7. The paste composition of claim 1, wherein the metal oxide comprises at least one metal oxide selected from the group consisting of titanium oxides, niobium oxides, hafnium oxides, indium oxides, tin oxides, zinc oxides, or a combination comprising at least one of the foregoing metal oxides.

8. The paste composition of claim 1, wherein the metal oxide has a nanostructure selected from nanotubes, nanowires, nanobelts, and nanoparticles.

* * * * *